United States Patent [19]

Jørgensen

[11] Patent Number: 5,382,574
[45] Date of Patent: Jan. 17, 1995

[54] INSULIN PREPARATIONS CONTAINING NICOTINIC ACID OR NICOTINAMIDE

[75] Inventor: Klavs H. Jørgensen, Virum, Denmark

[73] Assignee: Novo Nordisk A/S, Bagsvaerd, Denmark

[21] Appl. No.: 849,448

[22] PCT Filed: Dec. 20, 1990

[86] PCT No.: PCT/DK90/00335

§ 371 Date: May 20, 1992

§ 102(e) Date: May 20, 1992

[87] PCT Pub. No.: WO91/09617

PCT Pub. Date: Jul. 11, 1991

[30] Foreign Application Priority Data

Dec. 21, 1989 [DK] Denmark .............................. 6543/89
Jan. 10, 1990 [DK] Denmark ................................. 71/90

[51] Int. Cl.$^6$ ............................ C07K 7/40; C07K 7/42; A61K 37/26
[52] U.S. Cl. ........................................ 514/3; 514/4; 530/303
[58] Field of Search ..................... 514/314; 530/303

[56] References Cited

U.S. PATENT DOCUMENTS

| | | | |
|---|---|---|---|
| 2,179,384 | 11/1939 | Scott et al. | 514/4 |
| 2,538,018 | 1/1951 | Krayenbuhl et al. | 514/4 |
| 2,793,977 | 5/1957 | Caspe | 514/4 |
| 3,584,121 | 6/1971 | Krayenbuhl et al. | 514/4 |
| 4,971,951 | 11/1990 | Bellon et al. | 514/4 |
| 5,155,096 | 10/1992 | Bellon et al. | 514/4 |

Primary Examiner—Howard E. Schain
Attorney, Agent, or Firm—Steve T. Zelson; Karen A. Lowney

[57] ABSTRACT

Insulin preparations containing nicotinamide or nicotinic acid or a salt thereof shown interesting pharmacological properties.

19 Claims, No Drawings

INSULIN PREPARATIONS CONTAINING NICOTINIC ACID OR NICOTINAMIDE

The present invention relates to insulin preparations containing nicotinamide or nicotinic acid or a salt thereof. The preparations exhibit interesting therapeutic properties.

For decades, insulin has been used for the treatment of diabetics. Among the commercially available insulin preparations, rapidly acting, intermediately acting and prolonged acting preparations can be mentioned. Examples of rapidly acting preparations are neutral solutions of zinc containing insulin which, inter alia, are known under the trade marks Actrapid ® and Velosulin ®. Faster absorption of insulin compared to that obtained with the last-mentioned preparations can be effected by using monomeric or dimeric insulin analogs, vide European patent application No. 86306721, or by formulating insulin with magnesium salts, vide European patent application No. 87309229.

According to Diabetic Medicine 6 (1989), 568, diabetic patients have been treated orally with nicotinamide and they have been injected with insulin. The object of the study was to investigate whether small oral doses of nicotinamide would improve metabolic control. In this known study, nicotinamide and insulin was not mixed before administration. A similar study is described in Diabetologia 32 (1989), 160.

A composition for application to the hair and scalp which may contain nicotinamide and/or isophane insulin has been suggested in British patent No. 1,603,639. No compositions containing both nicotinamide and isophane insulin is described therein. This composition is for use in stimulating hair growth and in treating alopecia and excessive hair loss.

BRIEF DISCUSSION OF THIS INVENTION

According to this invention, a preparation containing nicotinamide or nicotinic acid or a salt thereof and insulin or an insulin derivative in solution is made. This preparation may, if desired, furthermore contain precipitated insulin or a precipitated insulin derivative having protracted action. For the purpose of subcutaneous administration, nicotinamide or nicotinic acid or a salt thereof is added in order to obtain a preparation with a more rapid onset of action. If the composition of this invention also contains precipitated insulin or a precipitated insulin derivative, a biphasic preparation may be obtained. Compared with the known biphasic insulin preparations, the biphasic preparations according to this invention have a more rapid onset of blood sugar lowering effect. Examples of precipitated insulin are zinc insulin crystals and protamine zinc insulin crystals.

The preparations of this invention are preferably solutions or suspensions.

Thus, the present invention relates to insulin solutions, optionally containing an insulin precipitate, for parenteral administration (for example, having a pH value in the range of about 3 to about 8.5) and containing nicotinamide or nicotinic acid or a salt thereof.

The concentration of dissolved insulin may be in the range of about 20 to 500 international units (IU) per ml.

Known to the art stabilizers and preservatives may be present in the insulin preparation.

ATTRIBUTES OF THIS INVENTION

Absent retarding substances in the insulin preparations of this invention, the absorption of insulin was surprisingly found to be faster than that of the reference insulin used in the examples below. This property is useful for a rapidly acting insulin, in particular in connection with a multiple injection regimen where insulin is given before each meal. With quicker onset of action, the insulin can conveniently be taken closer to the meal than with conventional rapidly acting insulin solutions. Furthermore, a faster disappearance of insulin probably diminishes the risk of post meal hypoglycemia.

The preparations of this invention are believed to be well suited for application in fountain pen like devices used for multiple injection insulin therapy.

DISCUSSION OF THIS INVENTION

The preparations of this invention may contain a naturally occurring insulin and/or an insulin derivative. Preferred insulins for practice of this invention are human insulin or a fast acting monomeric or dimeric insulin derivative, for example $Asp^{B10}$ human insulin. Preferably, insulin of high purity is used. Within the context of this invention, the term insulin when employed in a plural or generic sense is intended to encompass both naturally occurring insulins and insulin derivatives.

Some property differences can be expected to exist between the naturally occurring insulins and insulin derivatives.

The term derivatives of insulin (or insulin derivatives) comprises peptides having bloodsugar lowering effect and having an amino acid composition which is identical with that of human insulin with the proviso that a few of the amino acid residues are exchanged with other amino acid residues and, optionally, the C terminal carboxy group of the B chain is protected. Examples of such insulin derivatives are, inter alia, described in two European patent applications, publication Nos. 86301755 and 86306721, the content of which is hereby incorporated by reference. Insulin derivatives also comprise insulins and the above insulin analogs glycosylated in one or more of the positions A1, B1 and B29, e.g. with glucose, vide international patent application No. PCT/DK90/00062.

When human, porcine or bovine insulin is used for soluble preparations according to this invention, the zinc content of the insulin should preferably be below 6 zinc ions per hexamer insulin, more preferred below about 3 zinc ions/hexamer. However, if agents capable of forming complexes with zinc, such as citrate, are present, the content of zinc may be higher.

When insulin derivatives are used, the zinc content may not be critical to the same extent. In some cases of insulin derivatives, a high level of zinc ions (e.g. up to 10 zinc ions/hexamer) may be compatible with insulin solubilities under the conditions of the solutions according to this invention, and may even be desirable (vide European patent application No. 86301755).

The content of insulin in solutions of this invention may be in the range of 20 to 500 IU/ml, preferably in the range of 40 to 100 IU/ml, in preparations for injection. However, for other purposes of parenteral administration, the insulin content may be higher. The insulin solution may be mixed with a solid insulin material such as zinc insulin crystals or zinc protamine insulin crystals.

Salts of nicotinic acid may be formed with cations such as sodium, potassium and magnesium. The optimum concentration of such ions will depend on the salt(s) applied and should be chosen with regard to requirements for the desired timing of the preparation, the insulin solubility and the proximity of the composition to isotonic conditions. Examples of salts of nicotinamide are hydrochlorides. Other salts, amino acids, and non-ionic agents (besides preservatives) may be present if they are non-toxic and compatible with the insulin preparation as a whole.

According to this invention, the preferred concentration of nicotinamide plus salts thereof is in the range from about 0.01 to about 1 M, preferably from about 0.05 to about 0.5 M. The range of applicable concentration of nicotinic acid plus nicotinate is about 0.01 to about 0.5 M, preferably from about 0.05 to about 0.25 M. The upper limit is somewhat arbitrarily being chosen from the assumption that in some cases some overstepping of isotonicity may be acceptable.

The preservative present in the insulin preparation of this invention may be as in the heretofore conventional insulin preparations, for example phenol, m-cresol and methylparaben.

For preparation of aqueous insulin preparations according to this invention, a slightly acidic solution of insulin can be mixed with a solution containing all the other components of the final preparation. Then follows adjustment of pH value if required, stirring until a clear solution is obtained and finally sterile filtration. If desired, a sterile, protracted-acting insulin suspension may be added to the sterile insulin solution yielding a preparation with biphasic action. In order to protect the preparations from the denaturation that may take place-by occasional heating and shaking, known stabilizing agents, such as phospholipids, may be included.

Preparations containing an insulin derivative are prepared analogously.

The insulin preparations of this invention can be used in the treatment of diabetics by parenteral administration. It is recommended that the dosage of the insulin preparations of this invention which is to be administered to the patient be selected by a physician similarly to the selection of the dosage of known insulin preparations for injection to human beings.

This invention is further illustrated in the following examples which, however, are not to be construed as limiting.

Absorption Studies

The experiments described in the following examples were performed as absorption studies in pigs. Test and reference preparations (all solutions) were made from $125_I$-labelled human insulin or insulin derivative. 4 IU of the test preparation was injected at one side of the neck and 4 IU of the reference preparation at the other side in each of a number of pigs. The absorption was followed by external monitoring of the radioactivity remaining at the site of injection. The injections were performed by NovoPen TM, using either a normal needle, inserted to a depth of 6 mm (subcutaneously), or by a six-holed closed-end sprinkler needle (with the holes being distributed at distances between 4 and 10 mm from the hilt), inserted to the hilt. Injection of insulin by the latter type of needle is known to promote the absorption of insulin.

| Terms used in the examples | |
| --- | --- |
| $Zn^{++}$/hexamer: | Number of zinc ions per insulin hexamer. |
| $T_{75\%}$: | Time until 75% of initial radioactivity remaining. |
| $T_{50\%}$: | Time until 50% of initial radioactivity remaining. |
| $F_{75\%}$: | $T_{75\%}$ (test)/$T_{75\%}$ (reference). |
| $F_{50\%}$: | $T_{50\%}$ (test)/$T_{50\%}$ (reference). |

EXAMPLE 1 In this experiment, the number of pigs was 6 and the needle used was a normal needle.

The preparation of this invention was: 100 IU/ml zinc free human insulin, 0.15 M magnesium nicotinate, 0.05 g/l lysophosphatidylcholine myristoyl, and 2 g/l phenol; pH value: 6.4.

The reference preparation was Actrapid, 100 IU/ml human insulin, 3 $Zn^{++}$/hexamer, 16 g/l glycerol, and 3 g/l m-cresol; pH value: 7.3.

The results obtained was $F_{75\%}=0.56$, and $F_{50\%}=0.64$.

EXAMPLE 2 In this experiment, the number of pigs was 6 and the needle used was a sprinkler needle.

The preparation of this invention was: 100 IU/ml zinc free human insulin, 0.05 M magnesium nicotinate, 0.20 M nicotinamide, 0.05 g/l lysophosphatidylcholine myristoyl, and 1.2 g/l m-cresol; pH value: 6.2.

The reference preparation was Actrapid (as in Example 1).

The results obtained was $F_{75\%}=0.55$, and $F_{50\%}=0.69$.

EXAMPLE 3 In this experiment, the number of pigs was 11 and the needle used was a normal needle.

The preparation of this invention was: 100 IU/ml human insulin, 3 $Zn^{++}$/hexamer, 0.135 M sodium nicotinate, and 3 g/l m-cresol; pH value: 7.4.

The reference preparation was Actrapid (as in Example 1).

The results obtained was $F_{75\%}=0.67$, and $F_{50\%}=0.80$.

EXAMPLE 4 In this experiment, the number of pigs was 6 and the needle used was a normal needle.

The preparation of this invention was: 100 IU/ml zinc free human insulin, 0.3 M nicotinamide, and 1.2 g/l m-cresol; pH value: 7.5.

The reference preparation was Actrapid (as in Example 1).

The results obtained was $F_{75\%}=0.35$, and $F_{50\%}=0.54$.

EXAMPLE 5 In this experiment, the number of pigs was 6 and the needle used was a normal needle.

The preparation of this invention was: 100 IU/ml zinc free human insulin, 0.45 M nicotinamide, 0.05 g/l lysophosphatidylcholine myristoyl, and 1.2 g/l m-cresol; pH value: 7.4.

The reference preparation was Actrapid (as in Example 1).

The results obtained was $F_{75\%}=0.37$, and $F_{50\%}=0.60$.

EXAMPLE 6 In this experiment, the number of pigs was 6 and the needle used was a normal needle.

The preparation of this invention was: 100 IU/ml human insulin, 1.1 Zn++/hexamer, 0.3 M nicotinamide, 0.05 g/l lysophosphatidylcholine myristoyl, and 2 g/l phenol; pH value: 7.3.

The reference preparation was Actrapid (as in Example 1).

The results obtained was $F_{75\%}=0.60$, and $F_{50\%}=0.67$.

EXAMPLE 7 In this experiment, the number of pigs was 6 and the needle used was a normal needle.

The preparation of this invention was: 100 IU/ml human insulin, 3 Zn++/hexamer, 0.3 M nicotinamide, 0.05 g/l lysophosphatidylcholine myristoyl, and 2 g/l phenol; pH value: 7.4.

The reference preparation was Actrapid (as in Example 1).

The results obtained was $F_{75\%}=0.62$, and $F_{50\%}=0.78$.

EXAMPLE 8 In this experiment, the number of pigs was 6 and the needle used was a sprinkler needle in the preparation of this invention and a normal needle in the reference preparation.

The preparation of this invention was: 100 IU/ml human insulin, 1.1 Zn++/hexamer, 0.3 M nicotinamide, and 2 g/l phenol; pH value: 7.4.

The reference preparation was Actrapid (as in Example 1).

The results obtained was $F_{75\%}=0.45$, and $F_{50\%}=0.49$.

EXAMPLE 9 In this experiment, the number of pigs was 6 and the needle used was a normal needle.

The preparation of this invention was: 600 nM zinc free Asp$^{B10}$ human insulin (equivalent to 100 IU/ml human insulin), 0.3 M nicotinamide, and 3 g/l m-cresol; pH value: 7.3.

The reference preparation was 600 nM zinc free Asp$^{B10}$ human insulin, 16 g/l glycerol, and 3 g/l m-cresol; pH value: 7.3.

The results obtained was $F_{75\%}=0.57$, and $F_{50\%}=0.79$.

EXAMPLE 10 In this experiment, the number of pigs was 6 and the needle used was a normal needle.

The preparation of this invention was: 600 nM zinc free Asp$^{B10}$ human insulin, 0.25 M nicotinamide, 0.02 M magnesium chloride, and 3 g/l m-cresol; pH value: 7.4.

The reference preparation was 600 nM zinc free Asp$^{B10}$ human insulin, 16/1 glycerol, and 3 g/l m-cresol; pH value 7.3.

The results obtained was $F_{75\%}=0.47$, and $F_{50\%}=0.69$.

The features disclosed in the foregoing description and in the following claims may, both separately and in any combination thereof, be material for realising this invention in diverse forms thereof.

EXAMPLE 11 In this experiment, the number of pigs was 6 and the needle used was a normal needle.

The preparation of this invention was: 600 nM zinc free human insulin triglucosylated in position A1, B1 and B29, 0.3 M nicotinamide, 3 g/l phenol; pH value: 7.3.

The reference preparation was 600 nM zinc free human insulin triglucosylated in position A1, B1 and B29, 16 g/l glycerol, 3 g/l m-cresol; pH value: 7.4.

The results obtained was $F_{75\%}=0.54$, and $F_{50\%}=0.83$.

EXAMPLE 12 In this experiment, the number of pigs was 5 and the needle used was a normal needle.

The preparation of this invention was: 100 IU/ml zinc free human insulin, 0.15 M nicotinamide, 0.1 M NaCl, 0.05 g/l lysophosphatidylcholine myristoyl, 2 g/l phenol; pH value: 7.3.

The reference preparation was Actrapid (as in Example 1).

The results obtained was $F_{75\%}=0.70$, and $F_{50\%}=0.80$.

I claim:

1. Insulin preparation formulated for injection or infusion, the preparation comprising insulin or an insulin derivative and nicotinamide or nicotinic acid or a salt thereof.

2. The preparation according to claim 1, in which the content of nicotinamide plus salts thereof is in the range of from about 0.01 to about 1 M.

3. The preparation according to claim 2, in which the content of nicotinamide plus salts thereof is in the range of from about 0.05 to about 0.5 M.

4. The preparation according to claim 1, in which the content of nicotinic acid plus nicotinate is in the range of from about 0.01 to about 0.5 M.

5. The preparation according to claim 4, in which the content of nicotinic acid plus nicotinate is in the range of from about 0.05 to about 0.25 M.

6. The preparation according to claim 1 which further comprises zinc ions.

7. The preparation according to claim 6 which comprises less than about 6 zinc ions per hexamer insulin or insulin derivative.

8. The preparation according to claim 7 which comprises less than about 3 zinc ions per hexamer insulin or insulin derivative.

9. The preparation according to claim 1 in which the pH is above about 3.

10. The preparation according to claim 9 in which the pH is about 5 to about 8.5.

11. The preparation according to claim 10 in which the pH is about 6 to about 8.

12. The preparation according to claim 11 in which the pH is about 6.5 to about 7.5.

13. The preparation according to claim 1 which has an activity in the range of about 20 to about 500 IU per ml.

14. The preparation according to claim 13 which has an activity in the range of about 20 to about 200 IU per ml.

15. The preparation according to claim 14 which has an activity in the range of about 40 to about 100 IU per ml.

16. The preparation according to claim 1 which contains nicotinamide or a salt thereof, but does not contain nicotinic acid or a salt thereof.

17. The preparation according to claim 1 which contains nicotinic acid or a salt thereof, but does not contain nicotinamide or a salt thereof.

18. A method of treating diabetes which comprises administering to an individual in need of such treatment a preparation comprising insulin or an insulin derivative and nicotinamide or nicotinic acid or a salt thereof.

19. A method for making a preparation useful in the treatment of diabetes comprising admixing insulin or an insulin derivative with nicotinamide or nicotinic acid or a salt thereof, and formulating the admixture for injection or infusion.

* * * * *